United States Patent
Pameijer et al.

(10) Patent No.: US 6,688,763 B2
(45) Date of Patent: Feb. 10, 2004

(54) CURING LIGHT

(75) Inventors: Cornelius H. Pameijer, Simsbury, CT (US); George Zychek, Stratford, CT (US)

(73) Assignee: Jeneric/Pentron Incorporated, Wallingford, CT (US)

( * ) Notice: Subject to any disclaimer, the term of this patent is extended or adjusted under 35 U.S.C. 154(b) by 0 days.

(21) Appl. No.: 09/982,140

(22) Filed: Oct. 18, 2001

(65) Prior Publication Data

US 2003/0076693 A1 Apr. 24, 2003

(51) Int. Cl.⁷ .............................. A61B 1/07; A61C 13/15
(52) U.S. Cl. ...................... 362/573; 362/577; 362/804; 433/29
(58) Field of Search ................................ 362/572–574, 362/276, 109, 804, 577, 578, 579; 433/29

(56) References Cited

U.S. PATENT DOCUMENTS

| | | | | |
|---|---|---|---|---|
| 4,231,077 A | * | 10/1980 | Joyce et al. ............... 362/577 |
| 4,479,499 A | * | 10/1984 | Alfano ........................ 433/29 |
| 4,556,875 A | * | 12/1985 | Ishiwatari ................... 606/11 |
| 4,615,679 A | | 10/1986 | Wyatt ........................ 433/229 |
| 4,794,925 A | * | 1/1989 | Mori ........................... 607/93 |
| 4,797,794 A | | 1/1989 | Connor et al. ............. 362/226 |
| 4,907,133 A | * | 3/1990 | Nath ........................... 362/574 |
| 4,948,215 A | | 8/1990 | Friedman .................... 385/147 |
| 4,975,826 A | | 12/1990 | Bell ............................ 362/376 |
| 5,147,204 A | * | 9/1992 | Patten et al. ................. 433/29 |
| 5,298,758 A | | 3/1994 | Tateosian et al. ......... 250/492.1 |
| 5,302,124 A | | 4/1994 | Lansing ..................... 433/116 |
| 5,339,223 A | * | 8/1994 | Kremenchugsky et al. . 362/572 |
| 5,423,677 A | * | 6/1995 | Brattesani .................... 433/29 |
| 5,449,703 A | | 9/1995 | Mitra et al. .................. 522/57 |
| 5,628,556 A | * | 5/1997 | Hrabar et al. ............... 362/578 |
| 5,738,678 A | * | 4/1998 | Patel ........................... 433/29 |
| 5,749,724 A | | 5/1998 | Cheng ......................... 433/29 |
| 6,079,861 A | * | 6/2000 | Woodward et al. ......... 362/573 |
| 6,089,740 A | | 7/2000 | Forehand et al. ........... 362/573 |
| 6,159,005 A | | 12/2000 | Herold ........................ 433/29 |
| 6,325,623 B1 | * | 12/2001 | Melnyk et al. ............... 433/29 |
| 6,375,343 B1 | * | 4/2002 | Fujisawa et al. ............ 362/577 |
| 2002/0080611 A1 | | 6/2002 | Wood et al. ................ 362/263 |

* cited by examiner

*Primary Examiner*—Alan Cariaso
(74) *Attorney, Agent, or Firm*—Ann M. Knab

(57) ABSTRACT

A light curing unit comprising a light detecting panel positioned on the housing of the curing unit to allow the operator of the unit to visibly detect when the light is on. The panel is preferably part of the housing and is positioned proximate the light guide on the curing unit. It covers a section of the unit that exposes the light energy radiating from the lamp located in the housing of the unit. The panel is transparent or translucent, allowing the operator to see the light radiating from the lamp when the unit is in operation. If the unit is in operation and the light suddenly goes out, the operator can immediately detect that the light is out. The operator is then able to continue the curing operation with a new unit or lamp, without having to expend time using an ineffective curing unit.

6 Claims, 2 Drawing Sheets

CURING LIGHT

FIELD OF THE INVENTION

The present invention relates generally to a curing light for dental applications.

BACKGROUND OF THE INVENTION

Photocurable materials are commonly used in dentistry as sealants, adhesives, and condensable composite materials for filling dental cavities. To cure the photocurable materials, they are exposed to radiant energy in preselected spectral ranges in either the visible or ultraviolet spectrum. A light curing unit containing a reflector lamp is used to irradiate the photocurable material by directing light from the reflector lamp through a light guide positioned with its distal end adjacent to the photocurable material to be cured. The light guide functions to channel the light to the material at the site of the dental restoration.

The conventional light guide is a solid conductor of either glass or plastic, or is composed of a fiber optic conductor consisting of multiple strands of glass fiber held together as a flexible bundle or fused into a solid rod of individual fibers.

During use of the light guide, the light is positioned near the material to be cured and the light guide is turned on to initiate the curing process. The light guide is typically in the patient's mouth during the procedure and the tip of the guide is not clearly visible to the dentist or user of the light guide. Although the light guide is turned on and operating, the lamp in the light guide may be off because it is no longer useful and needs to be replaced, is not connected properly or is not working for some other similar reason. If this occurs, the operator of the unit is unable to detect this problem when the light guide is in the patient's mouth. This can disrupt the curing process and prolong the entire procedure.

It is desireable that the curing process of a dental material be continuous and efficient. It is preferable that the operator of a curing unit be able to easily detect when the light is not operating.

SUMMARY OF THE INVENTION

These and other objects and advantages are accomplished by the curing unit of the invention comprising a light detecting panel positioned on the housing of the curing unit to allow the operator of the unit to visibly detect when the light is on. The panel is preferably part of the housing and is positioned proximate the light guide on the curing unit. It covers a section of the unit that exposes the light energy radiating from the lamp located in the housing of the unit. The panel is transparent or translucent, allowing the operator to see the light radiating from the lamp when the unit is in operation. If the unit is in operation and the light suddenly goes out, the operator can immediately detect that the light is out. The operator is then able to continue the curing operation with a new unit or lamp, without having to expend time using an ineffective curing unit.

BRIEF DESCRIPTION OF THE DRAWINGS

Features of the present invention are disclosed in the accompanying drawings, wherein similar reference characters denote similar elements throughout the several views, and wherein.

DESCRIPTION OF THE INVENTION

The present invention is directed to a light curing unit having a hand held light guide for curing photoactivated dental restorative materials, resins, composites, coatings and the like such as Alert® condensable composite available from Jeneric/Pentron Inc., Wallingford, Conn. The unit may also be used for other procedures such as tooth whitening.

Figure 1:
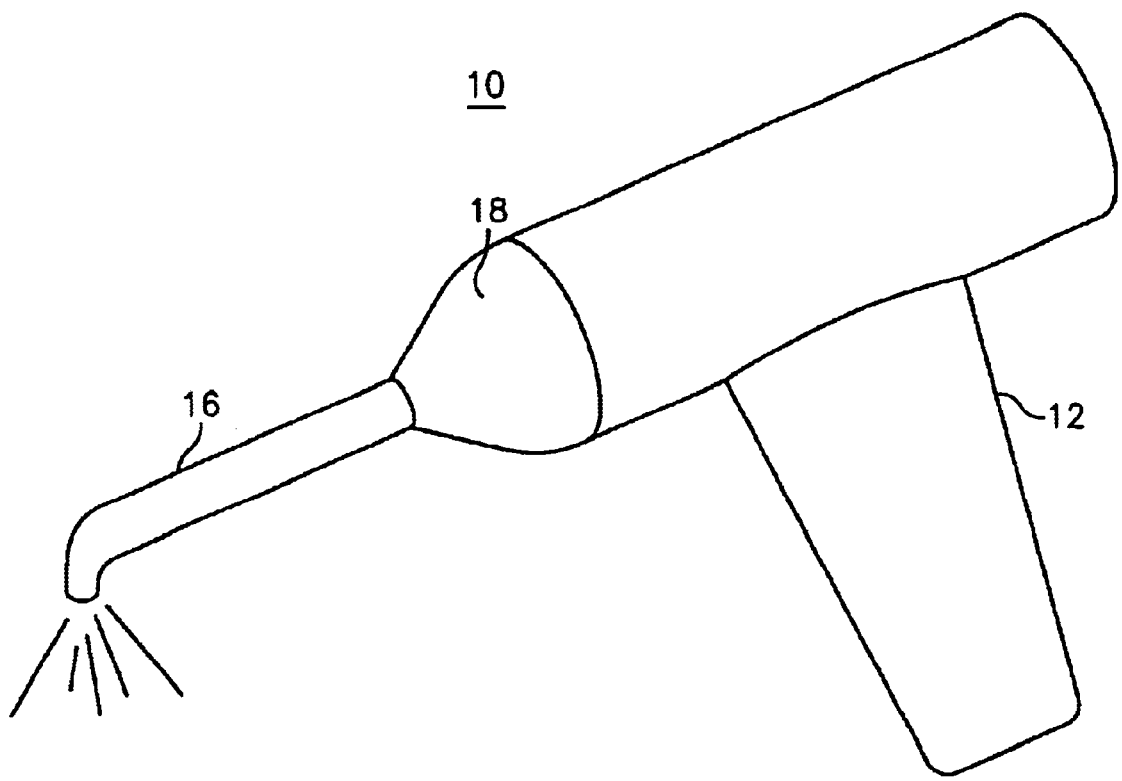
FIG. 1 is a perspective view of a light curing unit in accordance with the invention.
Figure 2:
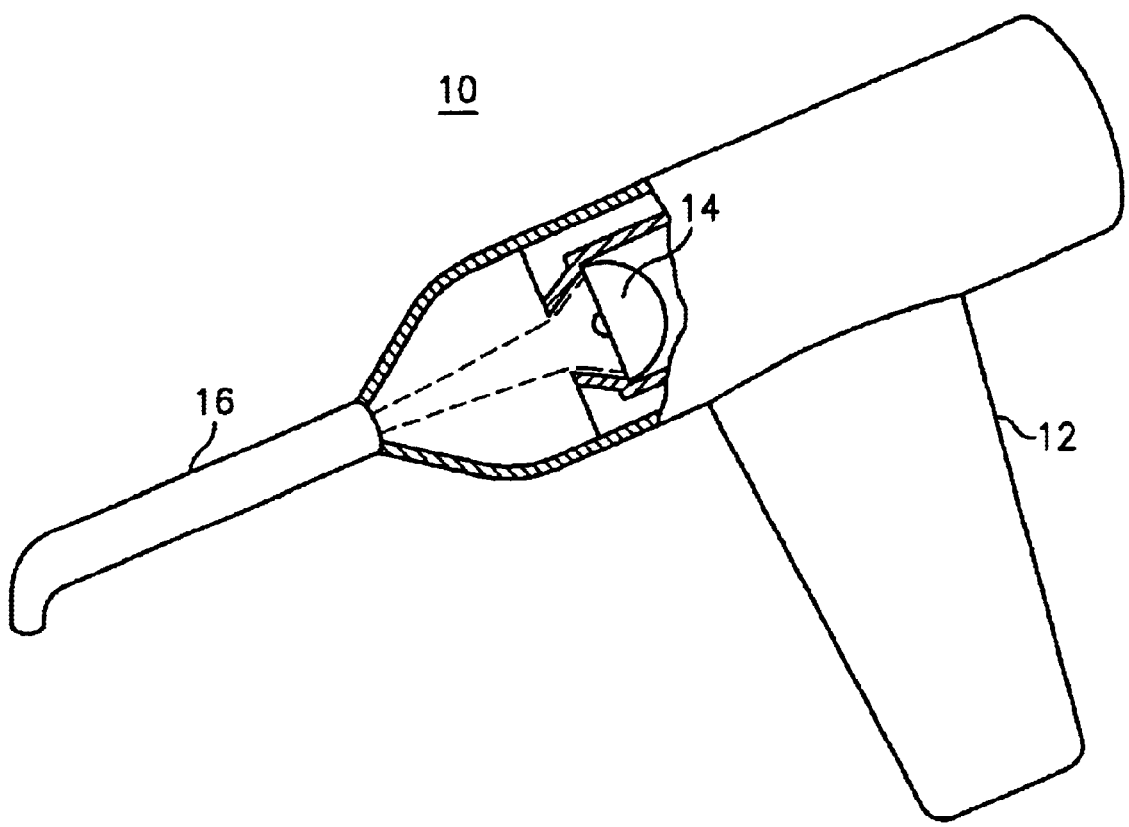
FIG. 2 is a perspective view showing a cut-away portion of the light curing unit of FIG. 1.

FIGS. 1 and 2 show a curing unit 10 in the form of a hand held light guide having a housing 12 containing a light source 14 therein. The light source supplies radiant energy to a light guide 16 and may be any light source such as a tungsten, halogen, mercury vapor, short arc xenon, metal halide or the like depending on the desired spectral bandwidth of radiant energy. Housing 12 includes a front panel 18 which attaches to housing 12 and completes the housing at the end of curing unit 10 at which end light guide 16 is inserted. Panel 18 is fabricated of a transparent or translucent material so that light can be detected through panel 18. Examples of clear or transparent materials include but are not limited to polycarbonate, polystrene, polymethylemethacrylate, polymethacrylate butadiene styrene, chlorinated polyvinylchloride, polyvinylidene chloride, and polyvinylidene fluoride. Examples of translucent plastics include but are not limited to low density polyetheylene, polybutylene, and high density polyethylene.

Panel 18 may be any shape or size that fits on housing 12. Panel 18 allows the user to see whether the light is on in curing unit 10 by visibly detecting the light through panel 18. This is critical during curing procedures, such as when the dentist is curing resin in the patient's mouth and cannot tell whether the light is on or not, since the light guide is directed on the resin in the patient's mouth. Typically the dentist inserts the light guide in the patient's mouth and turns the light on once it is in the mouth. Panel 18 allows the dentist to determine if the light is on and whether it continues to stay on. Should the light go off, the dentist can turn it on or replace it with a light that works. Panel 18 also acts as a protective filter to prevent harmful rays from permeating through the panel to protect the person using the curing unit.

As will be appreciated, the present invention provides a safe and effective way to detect the light in the curing unit and to determine whether it is on or off.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A light curing unit for curing photoactivated dental restorative materials, resins, composites and coatings comprising:

a housing wherein a radiant energy source is located;

a light guide inserted in the housing and operably connected to the radiant energy source;

wherein the housing comprises an external light detecting panel whereby light can be visibly detected therethrough by a user of the curing unit; and wherein the radiant energy source cures photoactivated dental restorative materials, resins, composites and coatings.

2. The light curing unit of claim 1 wherein the radiant energy source comprises a lamp selected from halogen, tungsten, mercury vapor, short arc xenon, or a metal halide.

3. The light curing unit of claim 1 wherein the light detecting panel is located proximate the light guide.

4. The light curing unit of claim 1 wherein the light detecting panel comprises a translucent or transparent material.

5. The light curing unit of claim 1 wherein the translucent material comprises polyethylene or polybutylene.

6. The light curing unit of claim 5 wherein the transparent material comprises polycarbonate, polystyrene, polymethylemethacrylate, polymethacrylate butadiene styrene, chlorinated polyvinylchloride, polyvinylidene chloride, or polyvinylidene fluoride.

* * * * *